United States Patent [19]

Osinga et al.

[11] Patent Number: 5,190,877
[45] Date of Patent: Mar. 2, 1993

[54] SACCHAROMYCES STRAINS FOR MALTOSE FERMENTATION

[75] Inventors: Klaas A. Osinga, Voorschoten; Robert F. Beudeker, Delft; Johannes B. Van der Platt, Leiderdorp; Johannes A. de Hollander, Oegstgeest, all of Netherlands

[73] Assignee: Gist-brocades N.V., Delft, Netherlands

[21] Appl. No.: 611,319

[22] Filed: Nov. 13, 1990

Related U.S. Application Data

[63] Continuation of Ser. No. 140,031, Dec. 31, 1987, abandoned.

[30] Foreign Application Priority Data

Sep. 3, 1987 [EP] European Pat. Off. ............ 87201670
Mar. 9, 1988 [EP] European Pat. Off. ............ 88200453

[51] Int. Cl.$^5$ .......................... C12N 1/19; A21D 2/00
[52] U.S. Cl. .................... 435/256; 435/940; 435/942; 435/172.3; 435/161; 435/320.1; 426/20
[58] Field of Search ............ 435/161, 172.3, 256, 435/940, 942; 935/21, 28, 33, 37, 59, 61, 69; 426/20

[56] References Cited

U.S. PATENT DOCUMENTS 4,778,761 10/1988 Miyanohara et al. ............ 435/320.1

OTHER PUBLICATIONS

Sreeknshna, et al. *PNAS USA* 82:7910-7913, 1985.
Needleman, et al. *PNAS USA* 81:2811-2815, 1984.
Hong, et al. *Gene* 41:75-84, 1986.
Nagata, et al. *EMBO J* 3(8):1825-1830, 1984.
Scherer, et al. *PNAS USA* 76(10):4951-4955, 1979.
Stewart "The genetic manipulation of industrial yeast" Canadian Journal of Microbiology 27:973-990. (181).
Gottlin-Ninfa et al., "Isolation and Functional Analysis of Sporulation-Induced Transcribed Sequences from *Saccharomyces cerevisiae*," MCB, 6(6):2185-2197 (Jun. 1986).
Riger et al., *Glossary of Genetics and Phylogenetics*, 4th Edition, New York (1976) p. 188.

*Primary Examiner*—Richard A. Schwartz
*Assistant Examiner*—Michelle Johnson
*Attorney, Agent, or Firm*—Barbara Rae-Venter

[57] ABSTRACT

Methods and compositions are provided relating to yeasts capable of improved fermentation of sugars. Particularly, genes from the MAL locus are used for transformation of yeast hosts, where the genes are under the wild-type promoter or a strong promoter which provides for regulatable or constitive expression under the conditions of fermentation. Particularly, the yeast hosts find use in the leavening of dough.

20 Claims, 16 Drawing Sheets

Sequence at promoter ADHI / maltose permease junction

5'--GCATACAATCAAGGAATTCCGGATCCTCTAGAGTCATCTAATTAACT-3'
        1              2           3            4    5

1. ADHI Promoter + 5' leader up to −15
2. Cloning linker
3. Part of pTZ19R polylinker
4. Part of EcoRV site
5. 5' leader sequence of maltose permease, starting at −9 sequence EF1αA         5'-----GTTTTAATTACAAA ATG CGT AAA GAG AAG TCT CAC ATT AAC GTT GTC G---3'
                                                            ⋮⋮⋮  ⋮⋮⋮ ⋮⋮⋮ ⋮⋮⋮ ⋮⋮⋮ ⋮⋮⋮ ⋮         ⎫
mutagenesis primer     3'CAAAATTAATGTTT TAC TGA TAA ACT CTA GAA GTG TAA TTG CAA CAG C 5'    ⎬ mutagenesis
                                                        ⌐⎯⎯⎯⎯⎯⎯⎯⌐                          ⎭ sequence maltase       5'---ATG ACT ATT TCT GAT CAT CCA G---3'
                           met thr ile ser asp his BclI : T|GATCA         ↓ = cleavage site
BglII: A|GATCT
                                                    met thr ile ser asp leu
                                                                        ↓
sequence pT4-m         5'-----GTTTTAATTACAAA ATG ACT ATT TCA GAT CTT CAC ATT AAC GTT GTC G---3'
                       ⎧⎯⎯⎯⎯⎯⎯⎯⎯⎯⎯⎯⎯⎯⎧ ⎧⎯⎯⎯⎯⎯⎯⎯⎯⎯⎯⎯⎯⎯⎧ ⎧⎯⎯⎯⎯⎯⎯⎯⎯⎯⎯⎯⎯⎯⎯⎯⎧
                         EF1αA 5' flank    five aminoterminal      EF1αA coding sequence
                                           codons of maltase
                                           gene; conversion
                                           BclI to BglII site
                                           (asterisks)

screening oligomer     5'GACTATTTCAGATCTT 3'

FIG. 7b

SACCHAROMYCES STRAINS FOR MALTOSE FERMENTATION

INTRODUCTION

This application is a continuation of U.S. application Ser. No. 07/140,031, filed Dec. 31, 1987, now abandoned.

Technical Field

The field concerns yeast used in the fermentation of sugars and processes for improving the strains.

Background

Yeast strains, for example the genus *Saccharomyces*, are capable of fermenting sugars to approximately equimolar amounts of carbon dioxide and ethanol under anaerobic conditions. The leavening action of yeast in dough is a result of this fermentation. The commercial product, baker's yeast, is available in various formulations, such as compressed yeast, fresh yeast or dried yeast. Dried yeast in turn is available as active dry yeast and as instant dry yeast with moisture contents of about 6-8% and 4-6%, respectively. The metabolism of sugars involves the transport of the sugars across the plasma membrane, for which specific enzymes are expressed by the yeast. Maltose uptake is dependent upon a specific maltose permease, where the maltose permease may exist in two forms distinguished by differences in maximal velocity ($V_{max}$) and Michaelis constant ($K_m$) (Busturia and Lagunis, *Biochim. Biophys. Acta* (1985) 820:324). The translocation of maltose across the yeast plasma membrane is coupled to an electrochemical proton gradient in the membrane, where for each maltose molecule taken up, one proton is symported (Serrano, *Eur. J. Biochem.* (1977) 80:97).

In comparison with the fermentation of glucose, two additional enzymes are required for the fermentation of maltose, vis. maltose permease and maltase ($\alpha$-glucosidase). The synthesis of these enzymes is induced by maltose and repressed by glucose, fructose, and mannose (Needleman et al., *Proc. Natl. Acad. Sci. USA* (1984) 81:2811). In non-sugared ("lean") doughs, maltose is the most abundant sugar available to yeast. Where sucrose is added to the dough, the sucrose is hydrolyzed extracellularly, and glucose and fructose are taken up by the yeast by action of distinct permeases.

It is generally found that addition of sucrose to media containing maltose, as for example dough, inhibits the metabolism of maltose by yeast cells. This is due to the fact that transcription of genes encoding maltose permease and maltase is repressed by glucose (R. B. Needleman, D. B. Kaback, R. A. Dubin, E. L. Perkins, N. G. Rosenberg, K. A. Sutherland, D. B. Forrest and C. A. Michels, *Proc. Natl. Acad. Sci. USA* (1984) 81:2811.

Genes required for the uptake and hydrolysis of maltose are clustered in the MAL-locus (Needleman et al., supra). *Saccharomyces* strains may contain up to 5 MAL-loci (MAL 1-4, 6), which are unlinked and located at the telomers of different chromosomes (Cenenza and Carlson, *Genetics* (1985) 109:661). A MAL-locus comprises the genes encoding maltose permease, maltase and one or more regulatory proteins (MAL regulator) required for the induction by maltose (Needleman et al., supra; Cohen et al., *Mol. Gen. Genet.* (1985) 200:1; Dubin et al., *Mol. Cell Biol.* (1986) 6:2757). These genes have been isolated and cloned (Cohen et al., *J. Bacteriol.* (1982) 149:1064). Maltose is produced in dough from starch by action of amylases, normally present in the flour. Other sugars may also be present in the flour in variable amount (0-0.5%), such as glucose, raffinose, etc. (Suomalainen et al., *Process Biochem.* (1972) 7:16). The sugars are rapidly consumed in yeast.

Studies have been performed to investigate the possible correlation between maltose fermentation and leavening activity of baker's yeast. While a positive correlation has been found between the rate of maltose fermentation with activities of maltase and maltose permease, this has not been observed in dough (Hautera and Lövgren, *J. Inst. Brew.* (1975) 81:309; Lövgren and Hautera, *Eur. J. Appl. Microbiol* (1977) 4:37).

Transformation of yeast cells with multicopy plasmids containing genes encoding maltase and maltose permease resulted in a 4-fold increase in specific activity of maltase but no enhancement of maltose permease activity. Transformation with genes encoding the regulatory protein resulted in a moderate increase in specific activity of maltase but no enhancement of maltose permease activity (Cohen et al., supra). No assays were performed for carbon dioxide or ethanol production and earlier studies would indicate that there would be an absence of correlation between the enzymatic activities of maltose permease and maltase with carbon dioxide production (leavening activity) in dough (Suomalainen et al., supra; Suomalainen, *Eur. J. Appl. Microbiol.* (1975) 1:1; Hautera and Lövgren, supra; Lövgren and Hautera, supra).

SUMMARY OF THE INVENTION

Methods and compositions are provided for improved leavening of dough by enhancing the uptake and/or initial metabolic conversion of transported substrates. Particularly, the yeast are transformed with genes coding for carrier proteins, saccharidases or sugar kinases, whereby particular sugars may be more rapidly and efficiently metabolized. The structural genes may be employed with the wild-type promoter or a heterologous promoter functional in the yeast host.

a) maltase and maltose permease genes. Arrow indicates direction of transcription. St (StuI) served as starting point for construction of deletion mutant. Relevant parts of sequence of intergenic area are shown below this map.

b) Sequence of pGb-m6g (Δ-9). Deleted area extends from -9 to -417. Polylinker refers to the oligonucleotides which have been ligated onto the Bal31-treated DNA (see also FIG. 4).

Figure 6A:
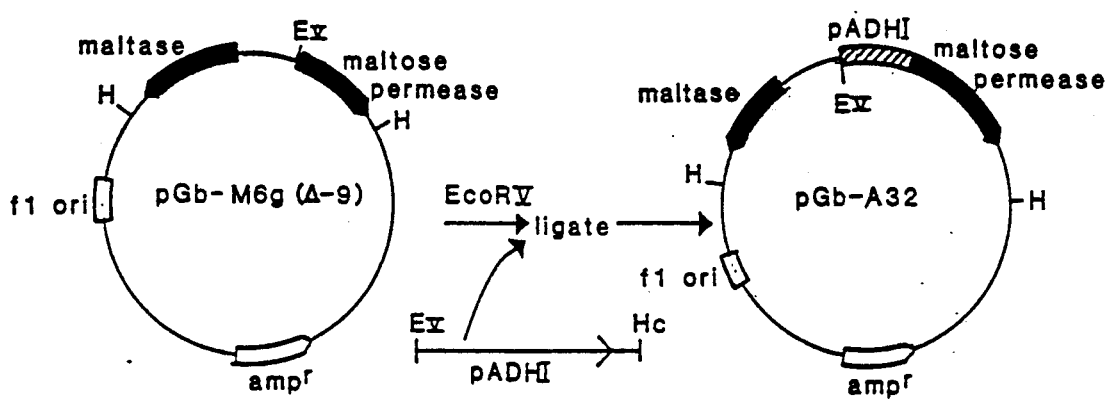
Figure 6B:
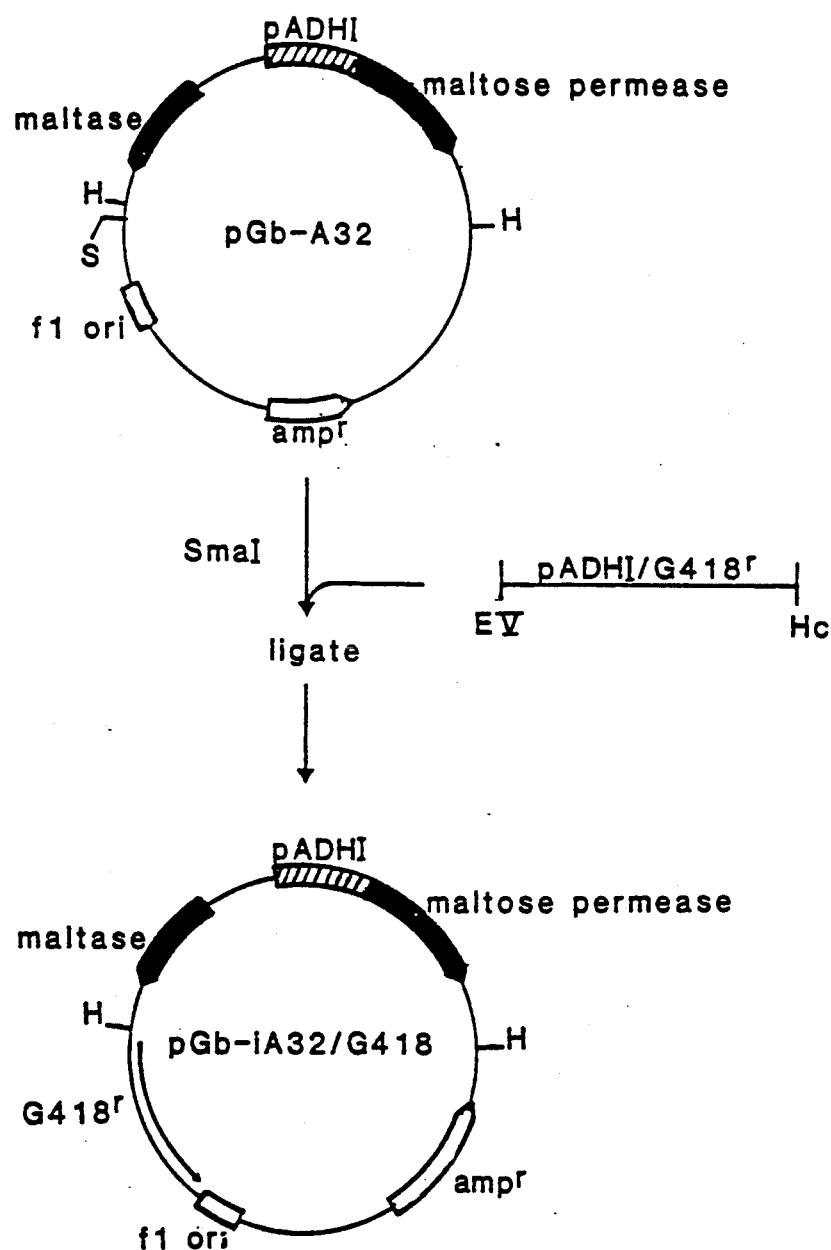

FIG. 6 (parts a and b) describes the construction of plasmid pGN-iA32/G418. Arrows indicate direction of transcription. Plasmids are drawn schematically and not to scale. Abbreviations: H, HindIII; EV EcoRV; f1 ori, origin of replication phage f1; amp, ampicillin resistance gene; G418, Tn5 gene (ADHI promoter) conferring resistance to G418; S, SmaI; Hc, HincII; pADHI, promoter alcohol dehydrogenase I gene +5' leader (hatched area).

Figure 7:
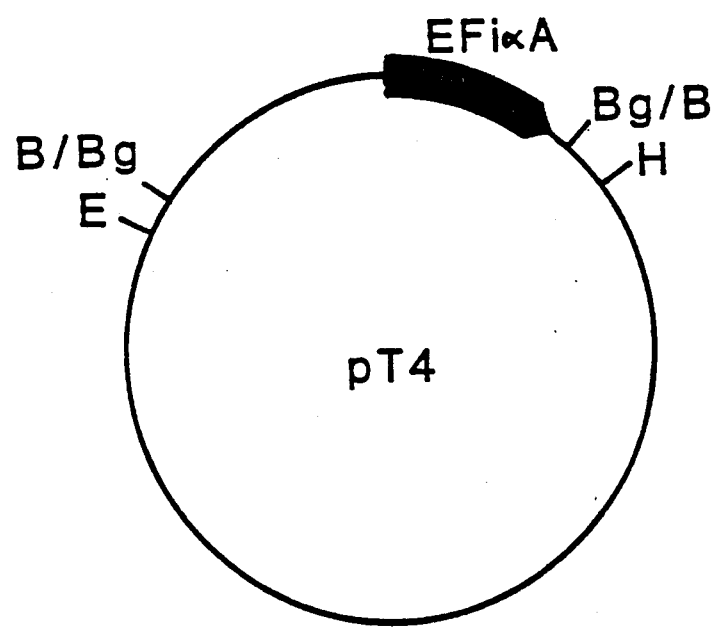

FIG. 7 (parts a-d) describes the construction of plasmid PGb-iRR01 a) plasmid pT4 is not drawn to scale. Abbreviations: E, EcoRI; B/Bg, BamHI/BglII ligation; H, HindIII;

b) mutagenesis on pT4 in order to fuse the EF1αA promoter +5' leader to the five N-terminal amino acid codons of the maltase gene in such a way that a BglII site is created as well. Relevant sequences are shown.

Mutagenesis primer is partly complementary (indicated with dots) to the EF1αA sequence. In the region of mismatches are the maltase codons and the -boxed-BglII recognition site (note that the presented orientation of the mutagenesis primer is 3'→5', i.e., the BglII site should be read from right to left (5'→3').

In the maltase sequence the N-terminal five amino acid codons are indicated. The BclI recognition site is boxed.

In the sequence of pT4-M, the sequence covering the mutation is shown. BglII site is boxed. Asterisks indicate the deviation from the maltase nucleotide sequence. The deviation in the fourth codon is a silent mutation.

c) Plasmids are not drawn to scale. Abbreviations: H, HindIII; Bc, BclI; E, EcoRI; Bg, BglII; EV, EcoRV; Bg/Bc, BglII/BclI ligation; pEF1αA (hatched box), 5' flank (promoter +5' leader sequence) of EF1αA; f1 ori, origin of replication of phage f1; amp, ampicillin resistance gene.

d) Plasmids are not drawn to scale. Abbreviations: see c).

Figure 8:
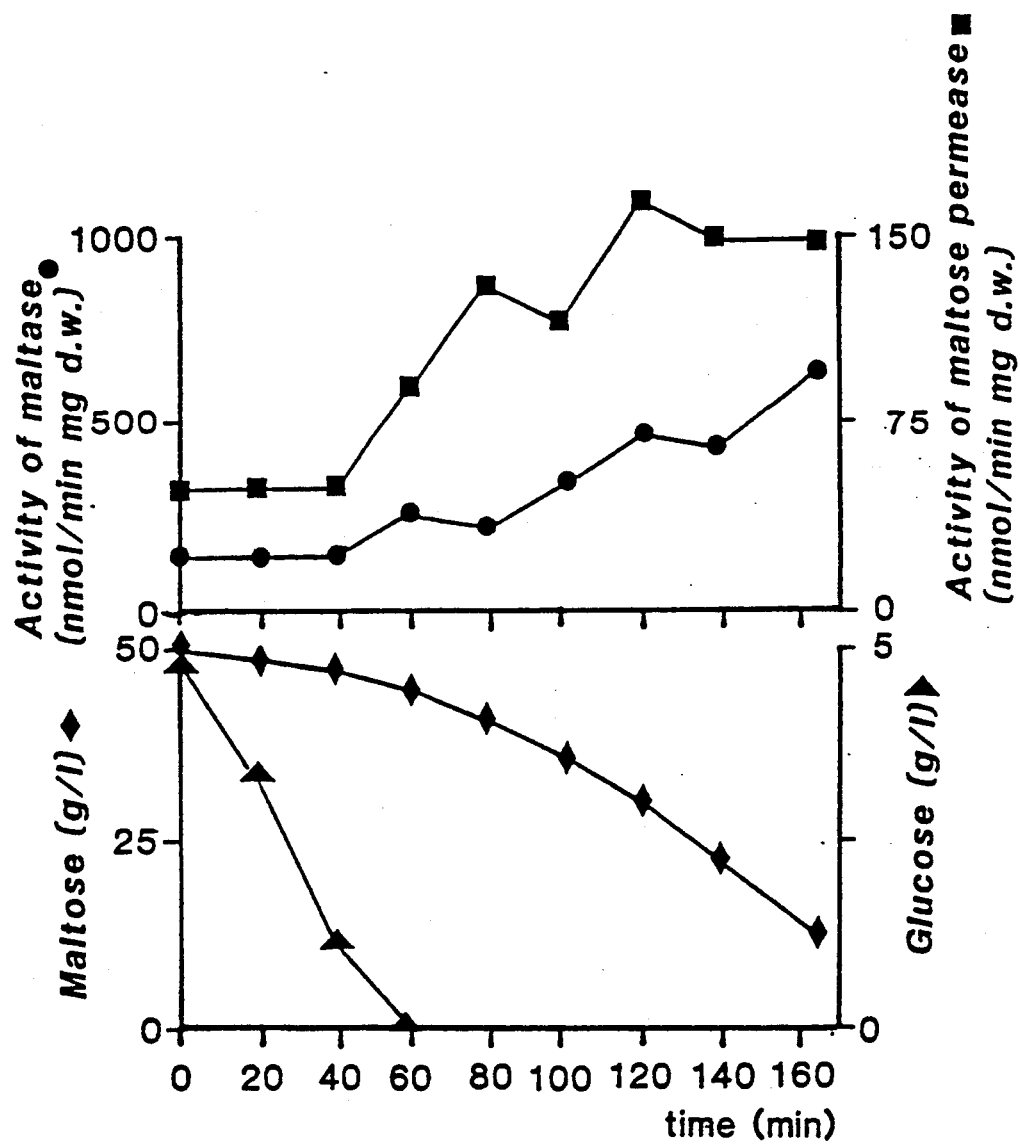

FIG. 8 describes the correlation between the increase in specific activity of maltose permease and maltase with the disappearance of glucose from medium A. Graphs are typical for commercial baker's yeast strains as for example strain A.

Figure 9:
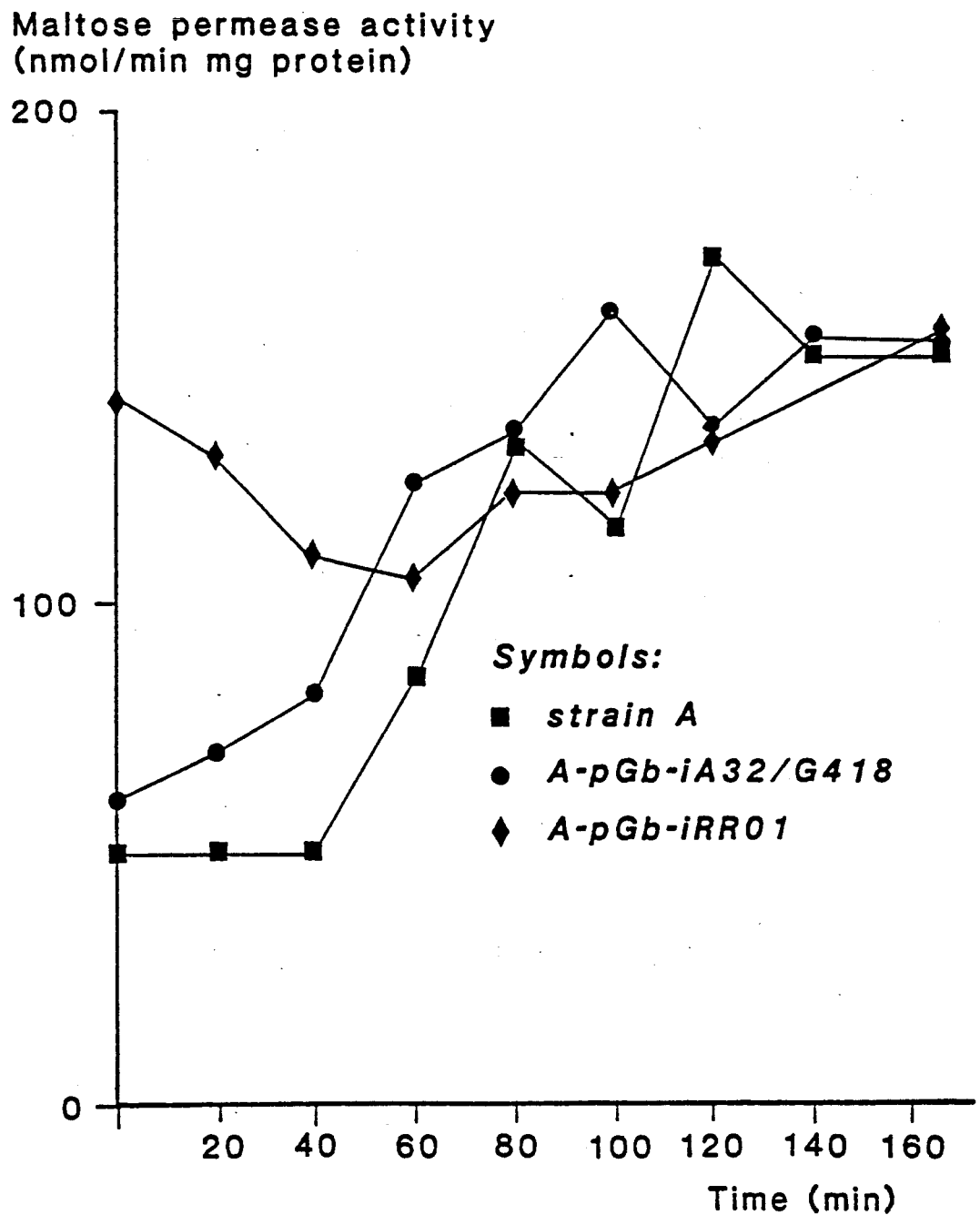

FIG. 9 describes the specific activities of maltose permease in strain A and its rDNA derivatives during a simulation of dough-rise in medium A.

Figure 10:
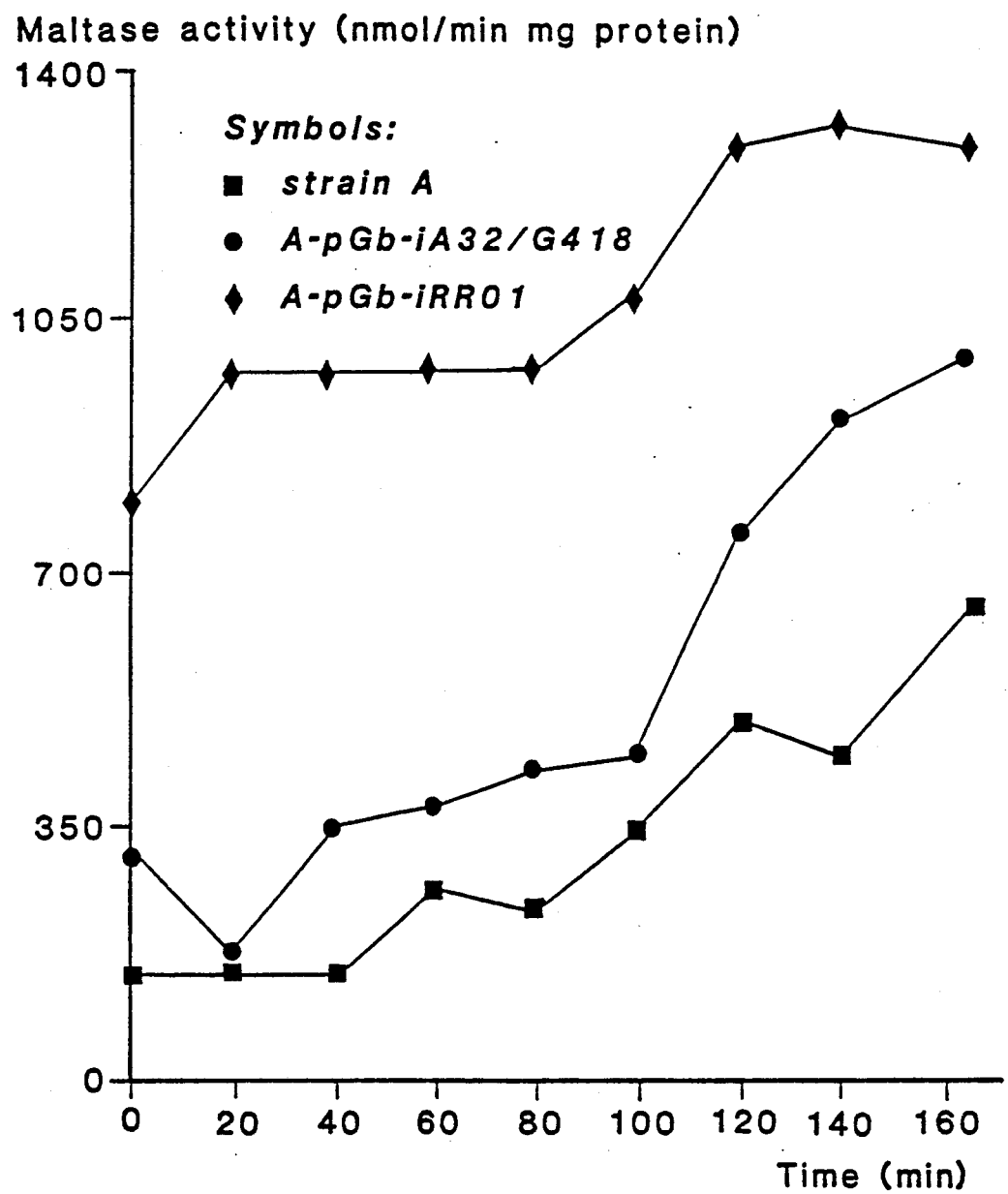

FIG. 10 describes the specific activities of maltase during a simulation of dough-rise by strain A and its rDNA derivatives in medium A containing maltose as main carbon and energy source.

Figure 11:
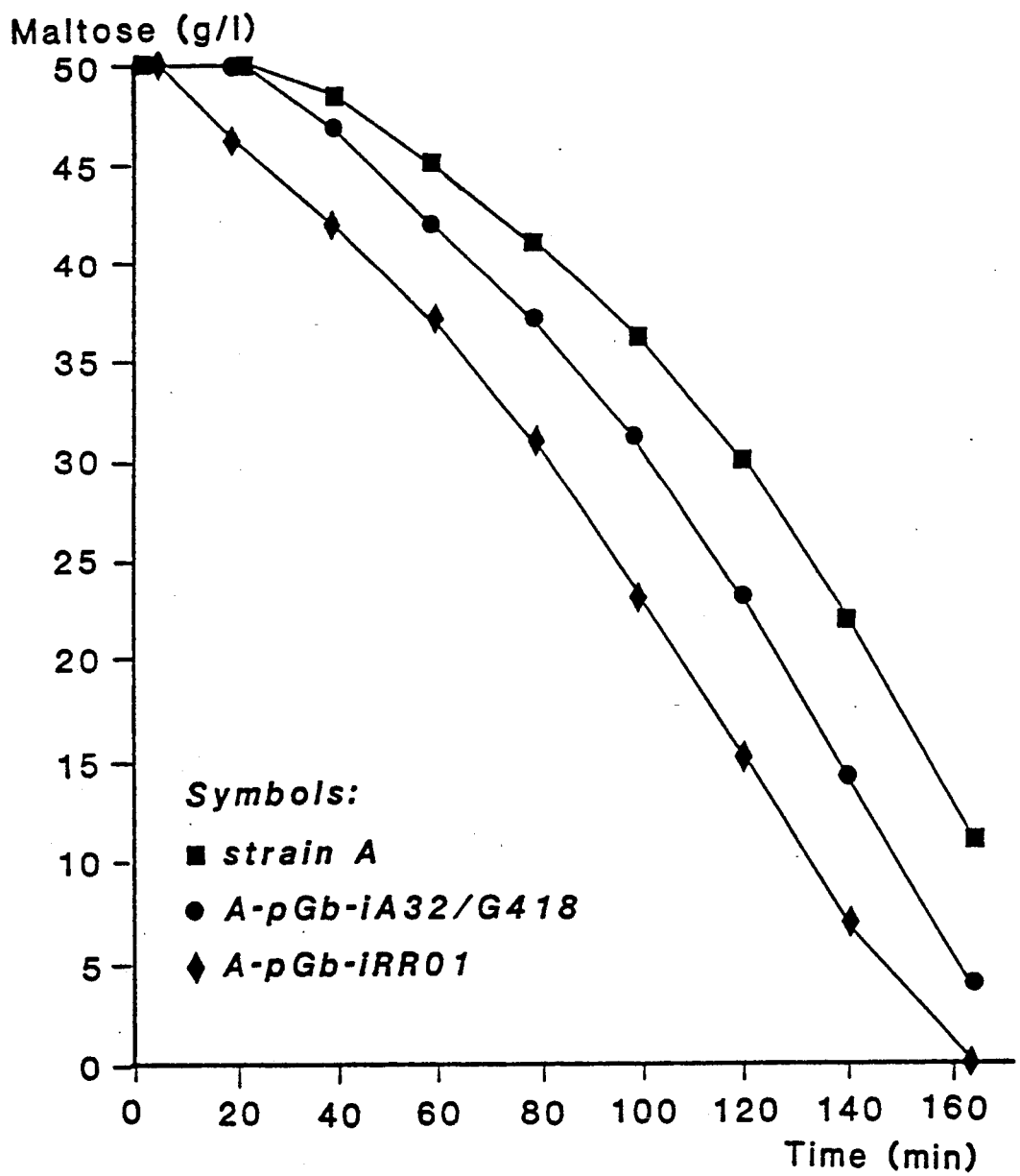

FIG. 11 describes the fermentation of maltose during a simulation of dough-rise by strain A and its rDNA derivatives in medium A containing maltose as main carbon and energy source.

Figure 12:
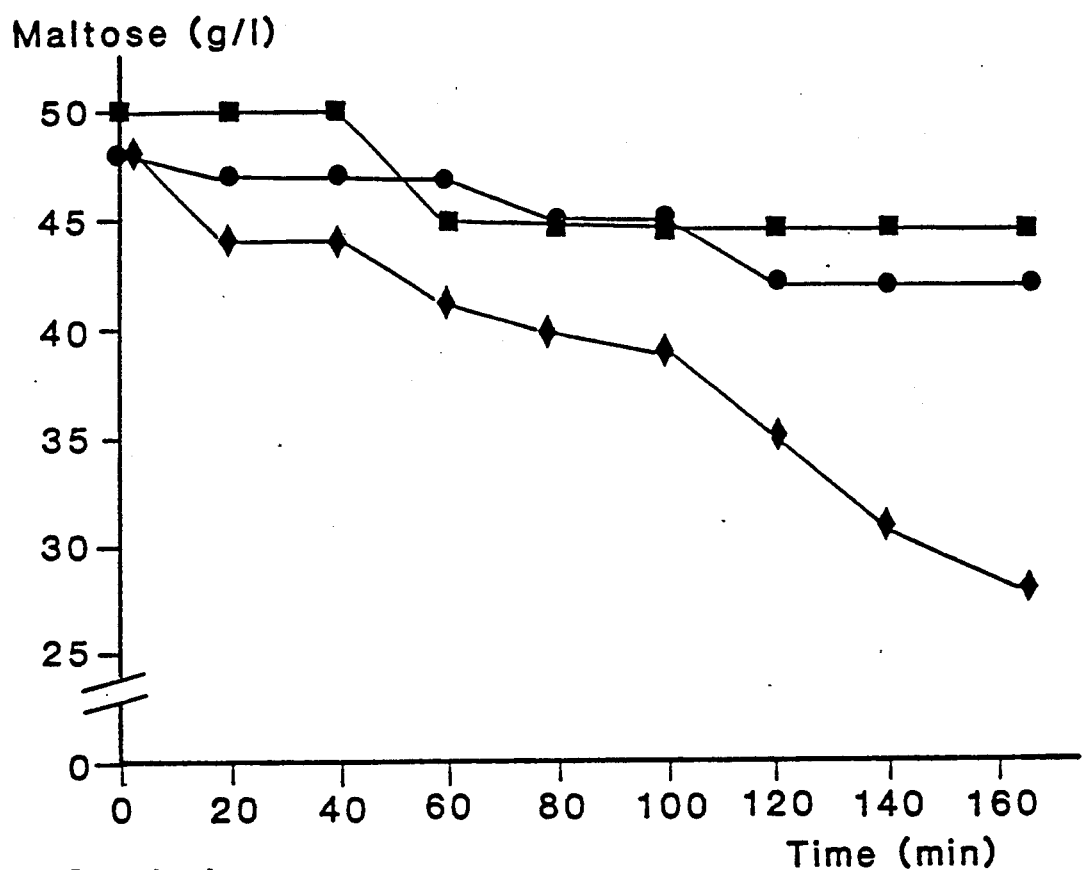

FIG. 12 describes the fermentation of maltose during a simulation of dough-rise by strain A and its rDNA derivatives in medium B containing glucose as main carbon and energy source.

LIST OF DEPOSITED STRAINS

The following strains have been deposited with the Centraal Bureau voor Schimmelcultures, Baarn, Holland:

Saccharomyces cerevisiae (Strain A) has been deposited with the CBS under the accession number 158.86 on Mar. 25, 1986;

Saccharomyces cerevisiae (Strain C) has been deposited with the CBS under the accession number 4-6.87 on Sep. 3, 1987;

Escherichia coli harbouring plasmid p21-40 has been deposited with the CBS under the accession number 400.87 on Aug. 29, 1987;

Escherichia coli harbouring plasmid pYEF46 has been deposited with the CBS under the accession number 401.87 on Aug. 29, 1987;

Escherichia coli harbouring plasmid pY6 has been deposited with the CBS under the accession number 402.87 on Aug. 29, 1987;

Escherichia coli harbouring plasmid peG418 has been deposited with the CBS under the accession number 160.86 on Mar. 25, 1986;

Escherichia coli harbouring plasmid pTZ19R has been deposited with the CBS under the accession number 405.87 on Sep. 3, 1987;

Escherichia coli harbouring plasmid pTZ19R/ADHI has been deposited with the CBS under the accession number 404.87 on Sep. 3, 1987;

Escherichia coli harbouring plasmid p153-215 AK has been deposited with the CBS under the accession number 403.87 on Sep. 3, 1987.

DESCRIPTION OF THE SPECIFIC EMBODIMENTS

Methods and compositions are provided which find use in the metabolism of sugars, particularly di- and higher polysaccharides. The methods and compositions have particular application in the leavening of dough, either lean or sweet dough. The methods and compositions involve the transformation of yeast hosts, so as to modify the capability of the yeast host in the metabolism of sugars, particularly as to those steps concerned with sugar transport across the plasma membrane and metabolism of the resulting sugar, involving hydrolysis of a polysaccharide, particularly a disaccharide, and/or a saccharide kinase, involved in phosphorylation of the sugar for further metabolic processing.

The subject invention may be employed with any of a number of yeast genera, including Saccharomyces, e.g., cerevisiae, baker's yeast, Schizosaccharomyces, Kluveromyces, e.g. lactis. These hosts may be modified by introducing genes which are homologous or heterologous to the host, where the genes may include a wild-type promoter or a promoter foreign to the gene, where the promoters are functional in the intended host.

The transformed hosts may have extrachromosomal elements incorporating constructs comprising one or more structural genes with their appropriate transcription and translational initiation and termination regions, where the extrachromosomal element may provide for stable maintenance or become integrated into the host genome. Various vectors are available which may be used for transformation of the yeast host.

The genes of interest include permeases, particularly maltose permease, saccharidases, particularly maltase, kinases, particularly hexokinases, and the like.

As indicated, the genes may be used with their natural or wild-type promoter or the promoter may be substituted with a different promoter. Particularly, where the wild-type promoter is regulatable or inducible, it may be desirable to provide for constitutive transcription, or a stronger or weaker promoter. Conversely, where the wild-type promoter is constitutive, it may be of interest to provide for a regulatable or inducible promoter or a stronger or weaker promoter.

Desirably, strong promoters will be employed, particularly where there may be a relatively low copy number of the construct in the host. Strong promoters will normally be those involved with the production of proteins produced at a high level during the life cycle of the yeast or where regulatable, at some period of interest in the life cycle of the yeast, as related to the subject invention.

Promoters associated with the glycolytic cycle of yeast are of particular interest, which include alcohol dehydrogenase I and II, phosphoglucoisomerase, glucose-6-phosphate dehydrogenase, triose phosphate isomerase, glyceraldehydephosphate dehydrogenase, phosphoglycerate kinase, enolas, phosphoglyceromutase, pyruvate kinase, and lactate dehydrogenase. Other promoters involved with proteins produced in high amount, include promoters associated with ribosomal expression, such as promoters for the transcription of initiation factors, elongation factors, and the like. Particular elongation factors include EF-1 and EF-2, etc.

Of particular interest is the use of heterologous promoters with structural genes involved with maltose metabolism, particularly maltase and maltose permease. These promoters may be constitutive or regulatable, so long as the promoter is induced during the fermentation of the sugar. For example, many of the glycolytic lean promoters are activated in the presence of a sugar or a sugar metabolite, such as ethanol. Thus, promoters such as alcohol dehydrogenase will be active during the leavening of flour. Similarly, those promoters associated with cell proliferation will also be active during the leavening of dough. Furthermore, by providing for promoters which are not regulated by the MAL regulator, the yeast may be used in the presence of glucose, without repression. In addition, the genes do not require maltose for induction.

Where the wild-type promoters are employed in conjunction with the structural genes of interest, it may be desirable to provide for enhanced production of a regulatory protein. In this way, the regulatory protein may be maintained at a high level, when the inducer is present. For example, in the presence of maltose, the MAL regulatory protein will be expressed at a high level, so as to provide for expression of the other proteins associated with maltose metabolism and regulated by the MAL regulator protein.

The subject host will have at least one copy of the construct, and may have two or more, usually not exceeding about 200, depending upon whether the gene is integrated into the genome, amplified, or is present on an extrachromosomal element having multiple copy numbers. Integration or non-integration may be selected, depending upon the stability required for maintenance of the extrachromosomal element, the stability of the particular extrachromosomal element prepared, the number of copies desired, the level of transcription available depending upon copy number, and the like.

The construct may include one or more structural genes with the same or different promoters. The construct may be prepared in conventional ways, by isolating the desired genes from an appropriate host, by synthesizing all or a portion of the genes, or combinations thereof. Similarly, the regulatory signals, the transcriptional and translational initiation and termination regions, may be isolated from a natural source, be synthesized, or combinations thereof. The various fragments may be subjected to endonuclease digestion (restriction), ligation, sequencing, in vitro mutagenesis, primer repair, or the like. The various manipulations are well known in the literature and will be employed to achieve specific purposes.

The various fragments may be combined, cloned, isolated and sequenced in accordance with conventional ways. After each manipulation, the DNA fragment or combination of fragments may be inserted into the cloning vector, the vector transformed into a cloning host, e.g. *E. coli,* the cloning host grown up, lysed, the plasmid isolated and the fragment analyzed by restriction analysis, sequencing, combinations thereof, or the like.

Various vectors may be employed during the course of development of the construct and transformation of the host cell. Thee vectors may include cloning vectors, expression vectors, and vectors providing for integration into the host or the use of bare DNA for transformation and integration.

The cloning vector will be characterized, for the most part, by having a replication original functional in the cloning host, a marker for selection of a host containing the cloning vector, may have one or more polylinkers, or additional sequences for insertion, selection, manipulation, ease of sequencing, excision, or the like. In addition, shuttle vectors may be employed, where the vector may have two or more origins of replication, which allows the vector to be replicated in more than one host, e.g. a prokaryotic host and a eukaryotic host.

Expression vectors will usually provide for insertion of a construct which includes the transcriptional and translational initiation region and termination region or the construct may lack one or both of the regulatory regions, which will be provided by the expression vector upon inertion of the sequence encoding the protein product. Thus, the construct may be inserted into a gene having functional transcriptional and translational regions, where the insertion is proximal to the 5'-terminus of the existing gene and the construct comes under the regulatory control of the existing regulatory regions. Normally, it would be desirable for the initiation codon to be 5' of the existing initiation codon, unless a fused product is acceptable, or the initiation codon is out of phase with the existing initiation codon. In other instances, expression vectors exist which have one or more restriction sites between the initiation and termination regulatory regions, so that the structural gene may be inserted at the restriction site(s) and be under the regulatory control of these regions. Of particular interest for the subject invention as the vector for expression, either for extrachromosomal stable maintenance or integration, are constructs and vectors which in their stable form in the host are free of prokaryotic DNA.

For extrachromosomal stable maintenance, it may be necessary to provide for selective pressure on those hosts maintaining the construct. Stable maintenance may be achieved by providing for resistance against a cytotoxic agent, e.g. an antibiotic, such as kanamycin or G418, or by imparting prototrophy to an auxotrophic host. For stable maintenance in a yeast host, the $2\mu$ origin or replication may be employed or a combination of a centromere, e.g. CEN3, and ars. For integration, generally homologous integration will be desirable, so that the construct will be flanked by at least about 50bp, more usually at least about 100bp on each side of the construct of a sequence homologous with a sequence present in the genome of the host. This sequence should be different from the locus of the construct of interest, where the structural gene exists in the yeast genome. For example, the flanking DNA would be other than the MAL locus, so as to provide for insertion of the construct at a site other than the MAL locus.

Vectors of particular interest comprise the $2\mu$ replicon, and at least one of a structural gene encoding for maltase, maltose permease, or a MAL regulatory gene, where the sequences encoding the proteins, may be under the wild-type promoter or under the transcriptional control of a non-wild-type promoter functional in yeast, particularly a promoter associated with a glycolytic enzyme, e.g. alcohol dehydrogenase I or II, or a gene associated with translation, e.g. elongation factor I or II. Of interest is the use of a DNA fragment comprising the maltase gene, the maltose permease gene and between the two genes, the wild-type divergent promoters.

The yeast host may be transformed in accordance with conventional ways. Conveniently, yeast protoplasts may be transformed in the presence of a fusogen, such as a non-ionic detergent, e.g. polyethyleneglycol. Once the host has been grown-up, it may then be further processed, depending upon its ultimate use. For example, with baker's yeast, it may be dehydrated, compressed, or processed in other conventional manner. The other yeasts may be harvested and used as hosts for commercial production of the expression product of other genes, where the hosts provide for efficient utilization of carbon sources by inducible regulation of growth.

Of particular interest for production of protein products, particularly heterologous protein products in the yeast host, are the use of industrial strains which are characterized by being prototrophic, inducing a high level of a protein product, either endogenous or exogenous, usually endogenous, refractory to transformation, particularly due to the presence of DNases secreted into the medium, and providing a robust growth pattern and ability to grow to relatively high density in large fermentors. For discussion of industrial yeast strains, see, for example, U.S. application Ser. No. 015,110, filed Feb. 17, 1987, whose disclosure is incorporated herein by reference.

Of particular interest is the use of yeast, more particularly baker's yeast, as a host in the subject invention for use with flour or dough. According to a preferred embodiment of the invention the novel strains will consume substantial amounts of maltose in the presence of glucose. Therefore bakers may save on sugar expenses as well, since less sugar needs to be added to obtain sweet doughs. The improved ethanol and/or carbon dioxide production results in less time or less yeast to develop lean dough, because of the improved leavening activity. In addition, since the maltose present in the flour may be metabolized, less sucrose or other sugar need be added to provide for a sweet dough. Furthermore, with an osmotolerant yeast host, the osmotolerant host may not only be employed with sweet doughs, but also lean doughs, since its capacity to ferment maltose has been enhanced. Thus, the same yeast may be used by bakers for both sweet and lean doughs.

The subject yeast transformants will provide significant advantages for production of potable and industrial alcohol. Also, the enhanced overall metabolic rate and the presence of maltose as a substrate, will enhance the production rate of metabolites, such as glycerol and aromatic compounds.

It is further found that the improvement in leavening activity is maintained during storage, even at elevated temperature, e.g. 20°-25° C. The transformants have substantially the same storage stability as their parental hosts. High sugar doughs do not adversely affect the advantageous properties realized with the subject transformants.

For integration, any convenient DNA sequence may be employed which is homologous with a sequence present in the yeast genome. For example, the construct containing genes from the MAL locus, may be inserted into a sporulation-specific gene (Gottlin-Ninga and Kaback, *Mol. Cell Biol.* (1986) 6:2185). A gene of interest may be inserted in lieu of the gene used by Gottlin-Ninja and Kaback (1986, supra). Upon transformation with a vector or base DNA comprising the construct, the construct will become inserted into the sporulation-specific sequences present in the host chromosome.

EXPERIMENTAL

The following experimental data are given to illustrate the invention. It is to be understood that a person skilled in the art who is familiar with the methods may use other yeast strains and vectors which can be equally used for the purpose of the present invention. These alterations are included in the scope of the invention.

Cloning Techniques

For general cloning techniques reference is made to the handbook of Maniatis et al. (Molecular Cloning, A Laboratory Manual (1982)). Restriction enzymes are used as recommended by the manufacturer and are obtained either from New England Biolabs (Biolabs), Bethesda Research Laboratories (BRL) or Boehringer Mannheim (Boehringer). In general 1 to 5 units of enzyme are needed to cleave 1 $\mu$g of DNA.

Transformation of *E. coli* was carried out using the $CaCl_2$-technique (Maniatis et al., supra).

Yeast Transformation

Transformation of yeast strains was carried out according to the method of Ito et al., *J. Bacteriology* (1983) 153:163–168. *Saccharomyces* is grown in a standard yeast nutrient medium to a density of 1 to 25, desirably 4 to 10 $OD_{610}$nm. The yeast cells are then harvested, washed and pretreated with chaotropic ions, particularly the alkali metal ions, lithium, cesium or rubidium, particularly as the chloride or sulphate, more particularly the lithium salts, at concentrations about 2 mM to 1.0M, preferably about 0.1M. After incubating the cells for from about 5 to 120 minutes, preferably about 60 minutes, with the chaotropic ion(s), the cells are then incubated with DNA for a short period of time at a moderate temperature, generally from about 20° C. to 35° C. for about 5 minutes to 60 minutes. Desirably, polyethylene glycol is added at a concentration of about 25 to 50%, where the entire medium may be diluted by adding an equal volume of a polyethylene glycol concentrate to result in the desired final concentration. The polyethylene glycol will be of from about 2000 to 8000 daltons, preferably about 4000 to 7000 daltons. Incubation will generally be for a relatively short time, generally form about 5 to 60 minutes. Desirably, the incubation medium is subjected to a heat treatment of form about 1 to 10 minutes at about 35° C. to 45° C., preferably about 42° C. For selection of transformants any useful marker may be used. Desirably, resistance to kanamycin and aminoglycoside G418 are of interest, the latter at a concentration of 200–300 $\mu$g/ml.

When yeast cells have been transformed with integrating plasmids, integration was directed to the MAL locus using BglII-digested DNA. The integrating plasmids used contain two BglII sites both in the maltase gene, 1.4kb from each other. This generates double-stranded breaks, which are recombinogenic and stimulate interaction with homologous chromosomal DNA. The gap is repaired form chromosomal information during the integration event (Orr-Weaver et al., *Proc. Natl. Acad. Sci. USA* )1981) 78:6354). The integration event yields one or a few copies of the plasmid vector (Szostak and Cou, *Plasmid* (1980) 2:536). The exact copy number in the transformants used in $CO_2$-production experiments has not been determined. The stability of the transformants is routinely checked by plating out samples on agar plates containing the antibiotic G418.

$CO_2$-Production Measurements a. In synthetic dough medium

Yeast cells were incubated in YEPMS medium (1% yeast extract; 2% bactopeptone; 3.75% maltose; 1.25% sucrose supplemented with 200 $\mu$g/ml G418). Growth was at 30° C. until late-log phase. Yeast cells were collected from 6 ml culture and resuspended in 8.8 ml synthetic dough medium. Composition of this medium (per L): saccharose 4.6 g; $(NH_4)_2SO_4$ 0.67 g; casamino acids 2.07 g; citric acid 4.02 g; $Na_3$ citrate 44.25 g; vitamin $B_1$ 9.2 mg; vitamin $B_6$ 9.2 mg; nicotinic acid 46 mg; caD(+)-pantothenate 18.2 mg; biotin 0.23 $\mu$g. For 10 minutes the suspension as allowed to equilibrate in a 28° C. waterbath, with moderate stirring after which time the flasks containing the yeast suspension were connected via a tube to a "gasburette." This burette was filled with a solution containing per liter 20 ml indicator solution (1 g methyl red; 0.5 g methylene blue; dissolved in 1 L 96% ethanol), 40 ml 1N $H_2SO_4$ and a trace of $CuSO_4$ (dissolved in $HNO_3$). The displacement of the volume of this solution in the burette is a measure of $CO_2$-production, which was measured during 165 minutes.

In each set of experiments values of $CO_2$-production obtained have been corrected for environmental temperature and pressure to standard conditions of 28° C. and 760 mm Hg, respectively. In addition, a correction was made for the amount of yeast. The colorimetric readings at 600 nm of the culture have been used as a correction factor in order to equalize the amount of yeast per $CO_2$ measurement.

b. In dough

The $CO_2$ gassing curves of compressed yeast was determined when fed batchwise on molasses, in dough with no sugar added (lean dough), or with 30% sugar. The lean dough was prepared as follows: 1 g of compressed yeast (containing 28.5% dry matter), 34 ml salt solution A (1.25 g NaCl dissolved in 34 ml of distilled water) and 62.5 g flour were mixed in a Hobart apparatus for 30 seconds at speed 1 and 2 minutes at speed 2 so as to obtain a well developed dough.

The 30% sugar dough contained 2.0 g of compressed yeast (of 28.5% dry matter), 34 ml salt solution B (0.928 g NaCl in 34 ml of distilled water), 62.5 g flour and 18.75 g sucrose (i.e. 30% sugar with respect to flour). Mixing was as for lean dough.

The dough was then transferred to a roundbottom flask. Gas-production measurement was started 7.5 minutes after mixing, by connecting the flasks containing the dough via a tube to a gasburette (see section a) and performed during 165 minutes at 28° C. In the event that the dry matter content of the compressed yeast differs from the value indicated above, the measured value of the $CO_2$ gassing power was then corrected by multiplying the $CO_2$ gassing power by the ratio of the required dry matter content to the actual measured value. In each set of experiments, values of $CO_2$ production obtained have been corrected for environmental temperature and pressure to 28° C. and 760 mm Hg, respectively.

Construction of Recombinant Plasmids 1) pGb-eMAL6g

Figure 1:
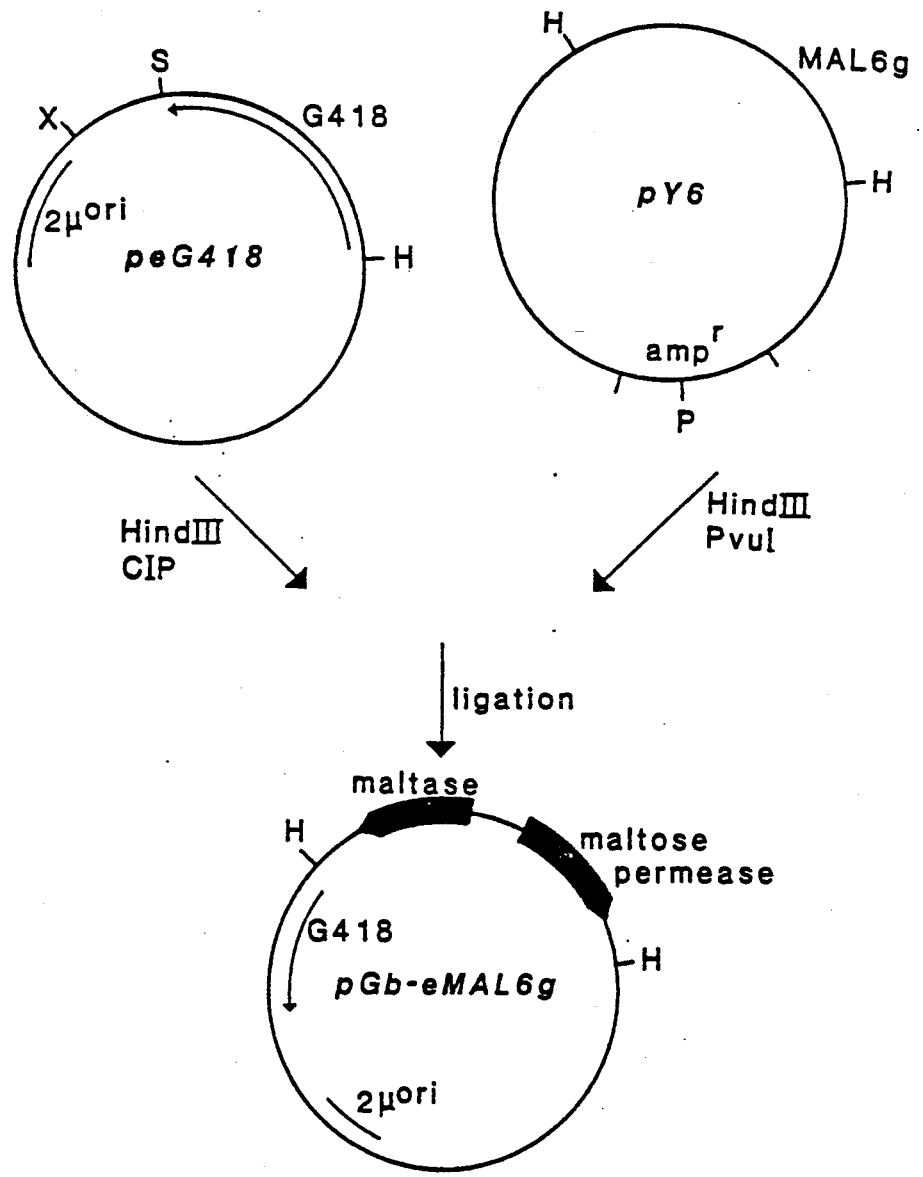
FIG. 1 describes the construction of plasmid pGB-eMAL69. Arrows indicate the direction of transcription of indicated genes. Plasmids are drawn schematically and not to scale. Abbreviations: G418, Tn5 gene (under control of ADHI promoter conferring resistance to G418); P, PvuI; X, XbaI; S, SalI; H, HindIII; CIP, calf intestine phosphatase.

This plasmid is capable of self-replicating in yeast and contains the genes encoding maltose permease and maltase. Its construction is outlined in FIG. 1.

peG418 is derived from pEMBLYe23 (Baldari and Cesarini, *Gene* (1985) 35:27) and contains between the SalI and HindIII sites a fragment with the Tn5 gene (Reiss et al., *EMBO J.* (1984) 3:3317) conferring resistance to G418 under direction of the promoter alcohol dehydrogenase I (ADHI) from yeast, similar to what was described by Bennetzen and Hall, *J. Biol. Chem.* (1982) 257:3018. peG418 was cleaved with HindIII, dephosphorylated with CIP and ligated with a digest of pY6 x HindIII, x PvuI. pY6 has been described (Needleman and Michels, *Mol. Cell. Biol.* (1983) 3:796; Needleman et al., *Proc. Natl. Acad. Sci. USA* (1984) 81:2811) and contains a 7.0kb HindIII fragment comprising the MAL6g locus. This yielded pGb-eMAL6g.

2. pGb-eMAL61

Figure 2:
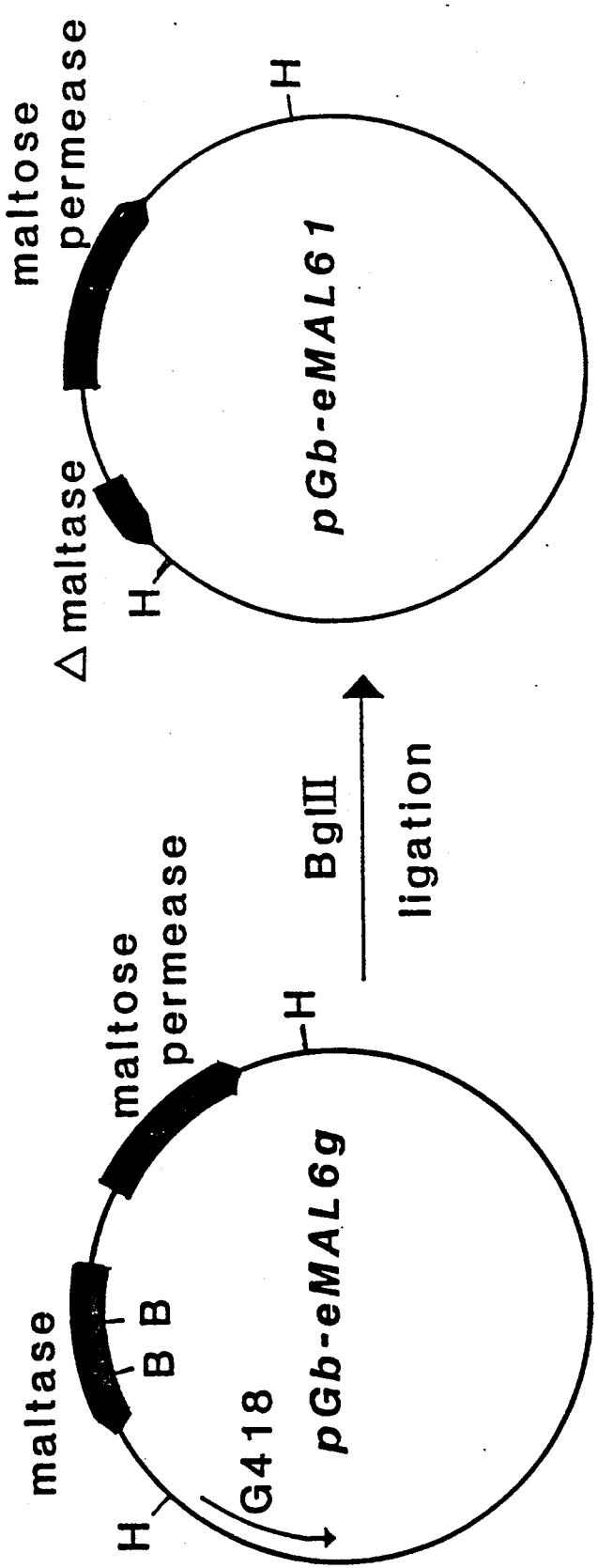
FIG. 2 describes the construction of pGB-eMAL61. Plasmids are drawn schematically and not to scale. Abbreviations: Δ maltase partial deletion maltase gene; B, BglI. See also the description of FIG. 1.

This $2\mu$ derived episomal plasmid contains the gene encoding maltose permease. Its construction is outlined in FIG. 2.

pGb-eMAL6g contains two BglII sites, both lying in the maltase gene. This 1.4kb BglII fragment was deleted from pGB-eMAL6g by digestion with BglII, followed by dilute religation to promote intramolecular ligation. Such a deletion has been shown to destroy maltase function (Cohen et al., *Mol. Gen. Genet.* (1985) 20:1).

3. pGb-eMAL63

This $2\mu$ derived episomal plasmid contains DNA covering the MALp function (regulatory protein gene or MAL-regulator). Its construction is outlined in FIG. 3.

From p21-40 (Needleman and Michels (1983) supra) the KpnI-SalI fragment was isolated containing the regulatory protein gene. This fragment was made blunt-ended using T4 DNA polymerase and the Klenow-DNA polymerase and thereafter cloned into the filled-in HindIII site of peG418.

4. pGb-M6g($\Delta$-9)

Figure 4:
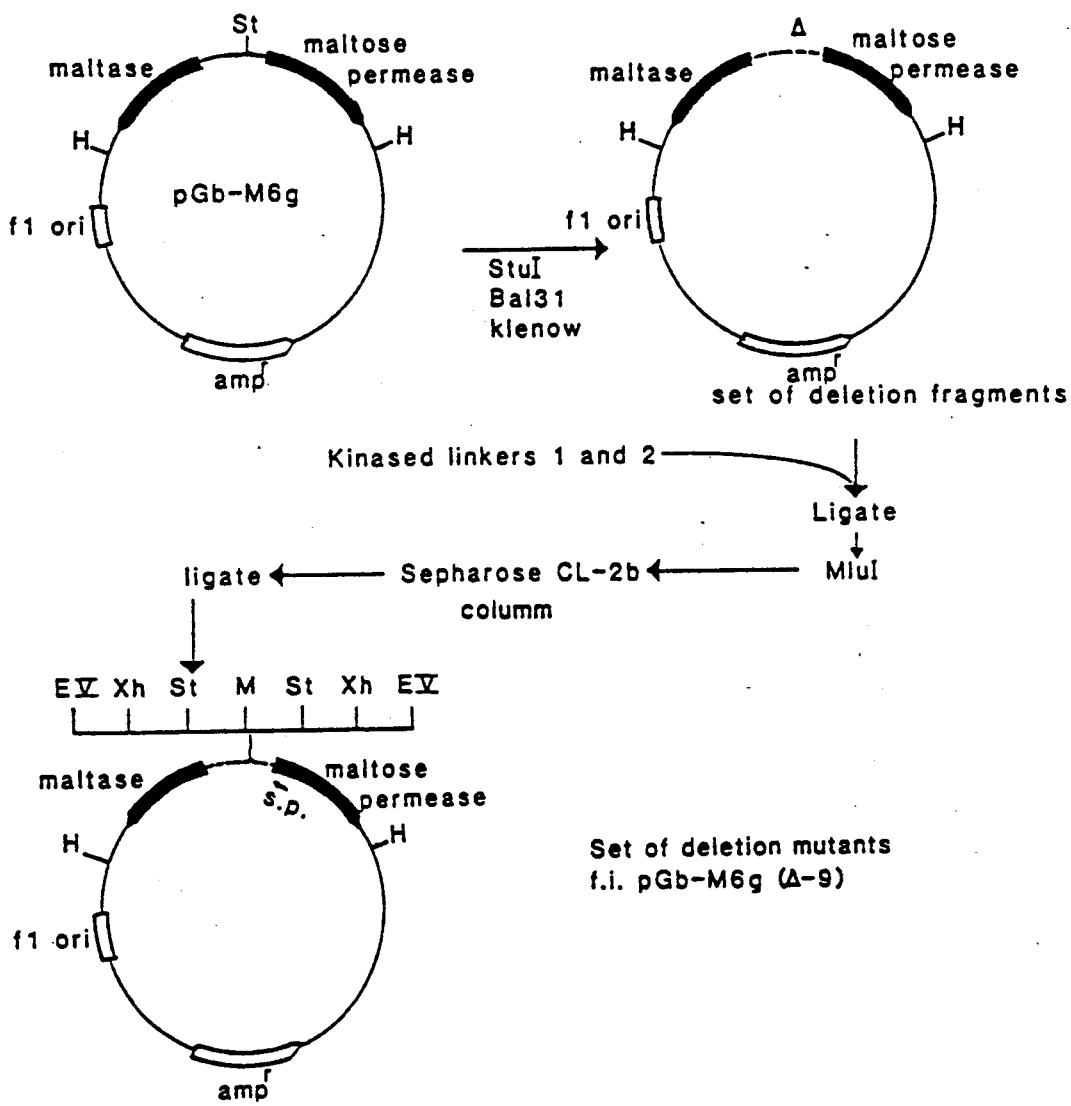
FIG. 4 describes the construction of pGM-M6g (Δ-9). Abbreviations: H, HindIII; St, StuI; Klenow, large fragment DNA polymerase I; EV, EcoRV; Xh, XhoI; M, MluI; f1 ori, origin of replication phage f1; amp, ampicillin resistance gene; s.p. sequence primer. Arrows indicate 5'→3' direction. Deleted area is indicated with dotted lines and Δ.

This plasmid is a promoter-deletion mutant made in the intergenic region of the divergently transcribed genes maltose permease and maltase (see FIG. 4). This region contains the promoters for both genes (Hong and Marmur, *Gene* (1986) 41:75). This deletion mutant has been made in order to replace the original promoters. The construction comprises the following steps:

a) The approximately 7.0kb HindIII fragment containing the genes for maltase and maltose permease (see also FIG. 1) was cloned into the HindIII site of pTZ19R. This plasmid is commercially available (Pharmacia). This results in pGb-M6g.

b) pGb-M6g was linearlized with StuI, which cuts in the intergenic region. The StuI generated ends served as starting point for the exonuclease Bal31 in order to nibble off parts of the promoters-containing intergenic area. StuI lies closer to the maltose permease gene (Hong and Marmur (1986) supra). the Bal31 incubation was carried out as described by Maniatis et al. (Maniatis et al. (1982) supra). At appropriate times samples were removed from the reaction and incubated with Klenow DNA polymerase to make blunt ends. Then synthetic linkers were ligated onto the ends containing several restriction sites.

The following complementary oligodeoxynucleotides have been used:

1. 5'GATATC CTCGAG AGGCCT A 3'
2. 3'CTATAG GAGCTC TCCGGA TGCGC 5'

In double-strand form restriction sites are created for EcoRV (GATATC), XhoI (CTCGAG), StuI (AGGCCT), and ligation at the sticky end creates the MluI site (ACGCGT). After kinase-reaction, the linkers have been ligated onto the Bal31 treated DNA, according to conditions as described (Maniatis et al., (1982) supra). The reaction mixture was then incubated with MluI and chromatographed through a 5 ml Sepharose Cl-2B column in order to separate the non-ligated oligodeoxynucleotides from the DNA fragment. Fractions containing this linear DNA were pooled, ligated to plasmid DNA and introduced into bacteria.

c) The resulting set of deletion mutants were subjected to sequence analysis. To this end, the double-stranded plasmids were converted into single-stranded DNA by superinfection with a helper phage (protocol according to recommendation by supplier). The single-stranded templates were extracted by normal M13 procedures for use in dideoxy sequencing (Sanger et al., *Proc. Natl. Acad. Sci. USA* (1977) 74:5463). As a primer the synthetic oligodeoxynucleotide (5'-GAATTC GGTAGCGTTCACGC-3') was used, which is complementary to a stretch of DNA near the ATG start codon of the maltose permease gene. Its orientation is such that the sequence is read towards the promoter (see also FIG. 4).

Figure 5:
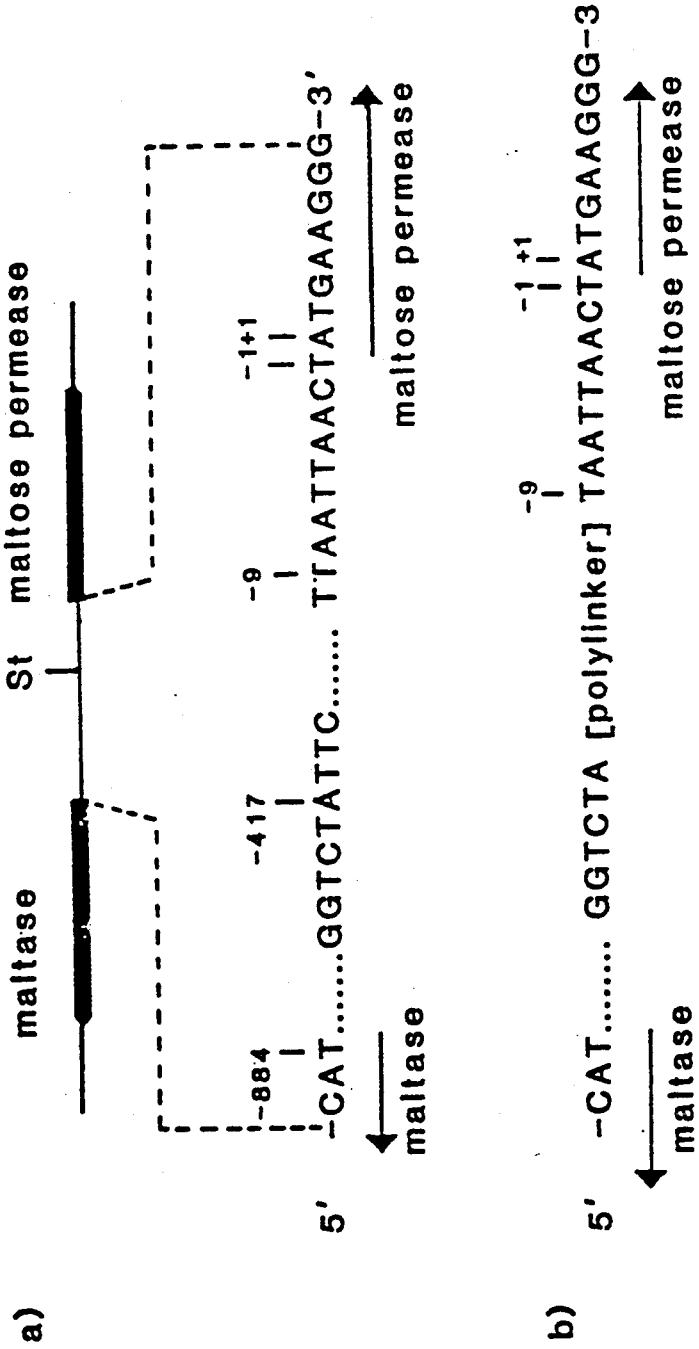
FIG. 5 describes the sequence of plasmid pGB-M6g (Δ-9).

The deletion mutant in which most of the maltose permease promoter had been removed, was selected for further experiments. Part of the maltase promoter is still present (note that the StuI site as startpoint for exonuclease treatment is located asymmetrically in the intergenic region). FIG. 5 lists the sequence at the deletion point of the mutant pGb-M6g(Δ-9). This is compared to the recently determined sequence of this entire area (Hong and Marmur (1986) supra). In the wild-type sequence, one difference has been observed with the published sequence: the C at -878 (numbering according to Hong and Marmur, (1986) supra), is not present in the subject sequence. In accordance, the DNA cannot be digested with HpaI or HincII at this position.

Plasmid pGb-M6g(Δ-9) is the starting plasmid to fuse other promoters to both the maltose permease gene and the maltase gene (see below).

5. pGb-iA32/G418

This plasmid is an integrating yeast plasmid. It contains the maltose permease gene, hooked onto the alcohol dehydrogenase I promoter and part of its 5' leader sequence. Its construction was as follows (FIG. 6).

a) Plasmid pTZ19R/ADHI contains a 1.4kb BamHI fragment with the ADHI promoter, starting at position -15 relative to the AUG codon (Bennetzen and Hall, *J. Biol. Chem.* (1982) 257:3018). From this plasmid, the 700bp EcoRV-HincII fragment was isolated and ligated to EcoRV digested pGb-M6g (Δ-9). Resulting plasmids were analyzed by restriction enzyme digestion and the proper orientation was confirmed via dideoxy sequence analysis on single-stranded templates (see FIG. 6). The same oligoprimer was used as described in section 4c.

As a result of the cloning procedure of the ADHI promoter fragment, part of the polylinker of pTZ19R (BamHI-HincII) is present between maltose permease gene and the ADHI promoter. The structure and sequence of pGb-A32 is shown in FIG. 6a.

b) Plasmid pGb-A32 was provided with the dominant selection marker G418R. A 1.9kb EcoRV/HincII contains the Tn5 gene conferring resistance to G418 under direction of the promoter alcohol dehydrogenase I. This fragment was isolated by an EcoRV/HincII double digestion of plasmid 153-215 AK (PLEASE DESCRIBE). The EcoRV/HincII fragment was cloned into the SmaI site of pGb-A32. This yielded pGb-iA32/G418.

6. pGb-iRRol

Figure 7C:
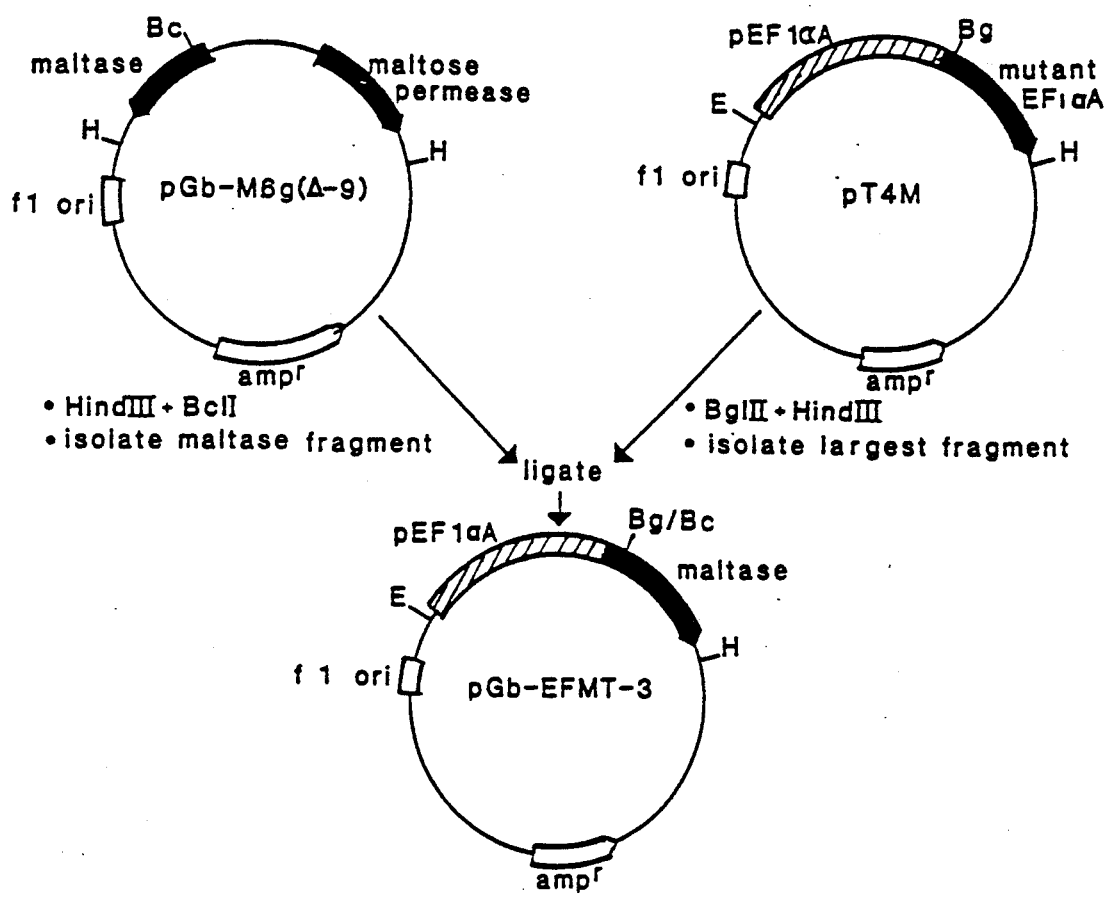
Figure 7D:
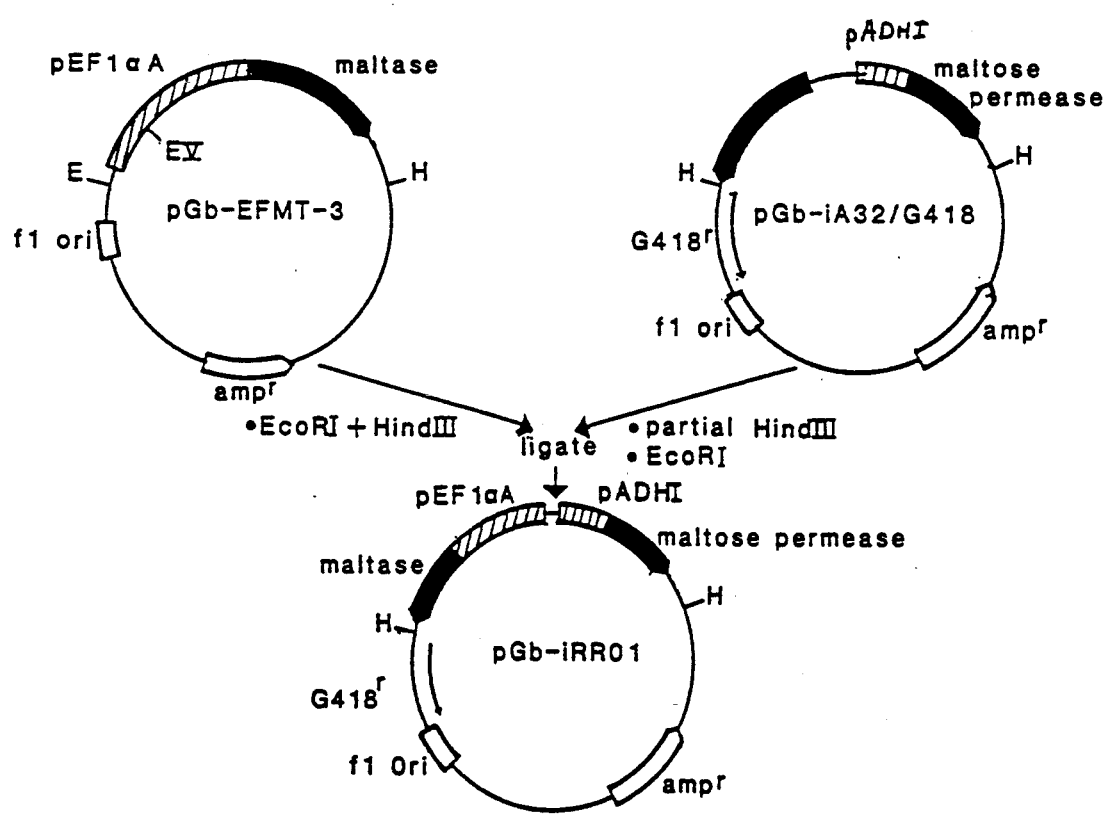

This plasmid is an integrating plasmid. It contains the maltose permease gene under direction of the promoter alcohol dehydrogenase I and the maltase gene under direction of the promoter of translation elongation factor EFlαA. The cloning pathway is depicted in FIG. 7. The approach was as follows: The maltase gene contains a BclI site around the fifth amino acid codon. Therefore, the EFlαA coding region was mutagenized in such a way that the first five amino acids became identical to those of the maltase protein. A BglII site was co-introduced at the position of the BclI site. Conversion of a BclI site to a BglII site is a silent mutation in the fourth codon. Via a BglII/BclI ligation the EFlαA promoter and leader sequence could be fused to the rest of the maltase gene. The procedure comprised the following steps:

a) The starting plasmid was pYEF46 (Nagata et al., *EMBO J.* (1984) 3:1825) which contains the entire gene coding for EFlαA. A 2.5kb BglII fragment covering this gene was isolated and cloned into the BamHI site of pTZ19R. Clone pT4 was picked (see FIG. 7a) and used for the oligodeoxynucleotide directed mutagenesis.

b) After superinfection with helper phage, single stranded ssDNA of pT4 was isolated. 400ng ssDNA, 400ng heat-denatured pTZ19R x BamHI and 100ng mutagenesis oligodeoxynucleotide (see FIG. 7b) were incubated in a volume of 10 µl of 7 mM Tris HCl pH 7.5; 50 mM NaCl and 7 mM MgCl$_2$ for 10 minutes at 56° C. After 10 minutes at room temperature, second strand synthesis and ligation were started by addition of 1 µl of Klenow DNA polymerase (2U). 1 µl TMD (200 mM Tris HCl pH 7.5, 100 mM MgCl$_2$, 100 mM DTT), 4 µl 2.5 mM dNTP-mix, 1 µl 10 mM ATP and 2 µl H$_2$O. The final volume was 20 µl. Incubation was performed for 16 hours at 17° C., after which time the mixture was transformed to *E. coli* JM101. Mutants were screened by colony hybridization with a kinased oligodeoxynucleotide, specific for the mutant (see FIG. 7b). This screening oligomer 5'-GACTATTT CAGATCTTC-3' was complementary to the introduced maltase codons and flanking necleotides. The hybridization was carried out for 16 hours in 6 x NET (1 x NET−0.15M NaCl, 0.015M Tris HCl pH 7.5, 0.001M EDTA) at 25° C. Post-hybridization washes were performed in the same mix at the same temperature (3 times 10 minutes), followed by a wash in 3×NET at 25° C. Several positive colonies were analyzed further. BglII digestion confirmed the presence of a BglII site. In addition, single-stranded DNA was isolated from a BglII site containing mutant (pT4-M) and subjected to dideoxy sequence analysis using a synthetic 17-mer primer, complementary to nucleotides 87–103 of the Efl$\alpha$A gene (Nagata et al. (1984) supra) (5'-CAATACCACCACACTTG-3'). The sequence obtained confirmed the successful introduction of the desired mutations.

c) The next step was to isolate the Efl$\alpha$A promoter/NH$_2$-terminal maltase gene segment from pT4-M and to fuse it via BglII/BclI sticky end ligation to the rest of the maltase gene. This step restores the maltase coding region downstream of the EFl$\alpha$A promoter and leader sequence (see FIG. 7c). Plasmid pGb-M6g ($\Delta$-9) was transformed to *E. coli* GM113, an *E. coli dam* strain, in order to be able to use the BclI site (which is methylation sensitive) (GM113: Thr−, leuB6, ProA2, Tris-4, metB1, lacY1, galK2, ara-14, tsx33, thi-1, thyA12, deoB16, supE44, rpsL260, dam3−). A 3.8kb BclI/HindIII fragment was isolated, containing the maltase gene except for the NH$_2$-terminal end. pT4-M was digested with BglII/HindIII and the large 4.1kb fragment isolated (EFl$\alpha$A promoter/NH$_2$ terminal and maltase gene). Both fragments were ligated to each other, resulting in pGb-EFMT-3. Sequence analysis confirmed the correctness of all introduced mutations.

d) Finally, pGb-EFMT-3 was digested with EcoRV and HindIII to purify a 4.8pb et al. promoter/maltase gene fragment. From pGb-iA32/G418 (see FIG. 6), an approximately 8.3kb HindIII (partial)/EcoRV fragment was isolated. This consists of the pTZ19R backbone, the ADHI promoter/maltose permease gene segment and the ADHI/G418$^R$ segment. Both fragments were ligated to yield pGb-iRRo1 (see FIG. 7d).

Enzymatic Analyses

The capacity to transport maltose by yeast cells was determined using [U-$^{14}$-C]-maltose at a concentration of 15 mM as a substrate at 30° C. Details have been published by R. Serrano supra. Maltase (E. C. 3.1.1.20) was assayed by using p-nitrophenyl-$\alpha$-D-glucopyranoside as a substrate in cell free extracts. The assay was carried out according to Halvorsen and Elas, *Biochim. Biophys. Acta* (1958) 30:28.

Substrate Consumption and Product Formation in Liquid Medium the disappearance of maltose and glucose from liquid media was quantitated using standard HPLC techniques. One liter of medium contained: 100 g maltose, 10 g glucose, 3.0 g (NH$_4$)$_2$SO$_4$, 4.0 g MgSO$_4$.7H$_2$O, 4 g KH$_2$PO$_4$, 4 g casamino acids (Difco), 4 g citric acid.-H$_2$O, 45 g trisodium citrate.2H$_2$O, 10 mg vitamin B$_1$, 10 mg vitamin B$_6$, 50 mg nicotinic acid, 20 mg Ca-D(+)-pantothenate and 0.02 mg biotin. The pH was adjusted to 5.7. Two ml of medium was added to a suspension of yeast (20 mg dry weight./2.0 ml of distilled water). This mixture, termed medium A, was incubated at 28° C. Medium B was like medium A but contained 20 times more glucose. The experiment was carried out under anaerobic conditions.

Protein Determination

Protein of cell-free extracts and of whole cells was determined by the microbiuret method of Goa, *J. Chim. Lab. Invest.* (1953) 5:218. Ovalbumin served as a standard.

Keeping Quality

Compressed yeast was stored in closed plastic containers at 23° C. during 4 days. Keeping quality is defined as the percentage of remaining gassing power after this period.

Manufacture of Compressed Yeast

A culture of a yeast strain was grown in a series of fermentors. Cells were cultivated in 10 L laboratory fermentors with a net volume of 6 L. During the fermentation pH and temperature was maintained at desired values by automatic control. The fermentation recipe used is based on procedures described by Butscheck and Kautzmann, Die Hefen, Band II Technologie der Hefen p. 501–591 (1962), Verlag Hans Carl, Nürnberg, FRG, and Reed and Peppler in Yeast Technology, the AVI Publishing Company Inc., Westport, Conn., USA (1973). The cultivation conditions of the final fermentation were:

molasses employed consisted of 80% by weight of beet molasses and 20% by weight of cane molasses, calculated on the basis of 50% sugar.

the required amount of phosphate was added in the form of mono-ammonium phosphate, prior to inoculation.

the temperature increased from 28° C. to 30° C. during the fermentation according to Table 1.

nitrogen was supplied during the fermentation as a 10% solution of NH$_3$ in water according to Table 1.

pH was kept at 5.0 during the first 8 hours of the fermentation and increased thereafter according to Table 1 to 6.2 at the end of the fermentation.

per kg of molasses containing 50% fermentable sugars, 12 mg of vitamin B$_1$ was added prior to inoculation.

The yeast obtained by this fermentation was concentrated and washed with tap water in a laboratory nozzle centrifuge. Yeast creams were compressed to a dry matter content varying between 26 and 32%.

The obtained protein content (% N×6.25) varied between 42–55% of dry weight as a consequence of different quantities of ammonia applied during the fermentation.

TABLE 1

Fermentation recipe used for the fed batchwise production of baker's yeast.

| Hours after inoculation | Molasses Supply (% of total amount added) | pH | T (°C.) | Ammonia supply (% of total amount used) |
|---|---|---|---|---|
| <0 | 7 | 5 | 28.0 | 0 |
| 0–1 | — | 5 | 28.0 | 0 |
| 1–2 | 5 | 4 | 28.0 | 0 |
| 2–3 | 6 | 5 | 28.5 | 1 |
| 3–4 | 8 | 5 | 28.5 | 7 |
| 4–5 | 8 | 5 | 29.0 | 11 |
| 5–6 | 8 | 5 | 30.0 | 11 |
| 6–7 | 10 | 5 | 30.0 | 12 |
| 7–8 | 10 | 5 | 30.0 | 15 |

TABLE 1-continued

Fermentation recipe used for the fed batchwise production of baker's yeast.

| Hours after inoculation | Molasses Supply (% of total amount added) | pH | T (°C.) | Ammonia supply (% of total amount used) |
|---|---|---|---|---|
| 8–9 | 10 | 5.3 | 30.0 | 17 |
| 9–10 | 10 | 5.6 | 30.0 | 17 |
| 10–11 | 10 | 5.9 | 30.0 | 10 |
| 11–12 | 8 | 6.2 | 30.0 | 0 |

EXAMPLE 1

$CO_2$ production of yeast transformed with 2μ derived plasmids containing genes derived form the MAL6 locus.

Figure 3:
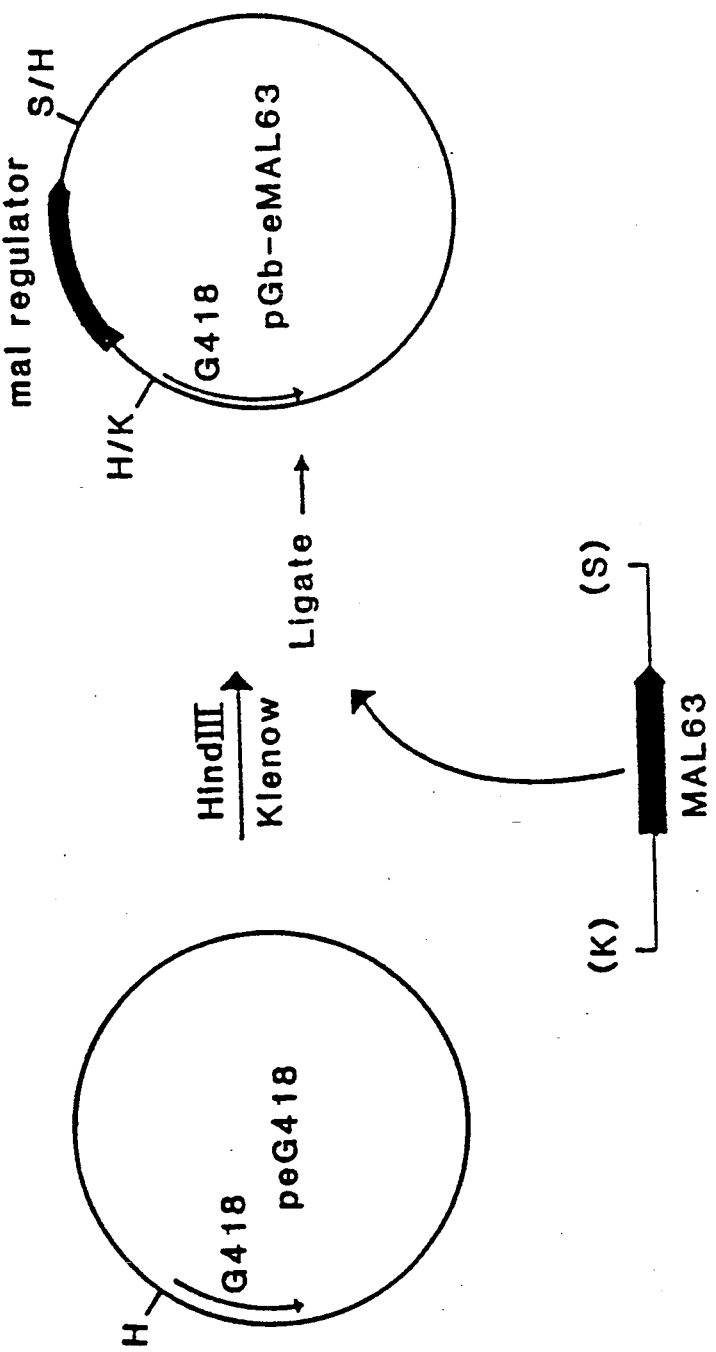
FIG. 3 describes the construction of plasmid pGB-eMAL63. Plasmids are drawn schematically and not to scale. Abbreviations: (K), filled-in KpnI site, (S), filled-in SalI site; Klenow, large subunit DNA polymerase; H, HindIII. See also description of FIG. 1.

Commerical baker's yeast strains A and C were transformed with pGb-eMAL6g (maltose permease and maltase, see FIG. 1), pGm-eMAL61 (maltose permease, see FIG. 2) and pGb-eMAL63 (MAL-regulator, see FIG. 3). The MAL genes still contain their original promoters. The nomenclature is as follows: ApeG418 denotes strain A transformed with peG4118. The effects of these plasmids on the $CO_2$ production in synthetic dough medium is summarized in Table 2. The host strains, transformed with the precursor plasmid peG418 (see FIG. 1), serves as a reference, since the mere presence of a multicopy plasmid has a negative effect on the gas production.

All transformants display major $CO_2$ production improvements, relative to the control. The combination of extra copies of both maltose permease and maltase genes gives the highest enhancement, about 40% in strain A and 18% in strain C.

Transformants ApGb-eMAL6g and CpGb-eMAL6g have also been tested in dough with no added sugar. In this case the yeast was grown fed batch-wise on molasses.

Again, major improvements in $CO_2$ production were obtained (Table 3).

TABLE 2

Gas production of strain A and strain C transformed with 2μ derived MAL plasmids, relative to the vector-transformed strains. $CO_2$ production was measured in synthetic dough medium (see experimental procedures) and corrected to 285 mg dry matter. Data are mean values of several experiments.

| Strains | 100 minutes | 165 minutes |
|---|---|---|
| ApeG418 | 100 | 100 |
| ApGb-eMAL6g | 157 | 141 |
| ApGb-eMAL61 | 144 | 123 |
| ApGb-eMAL63 | 119 | 115 |
| CpeG418 | 100 | 100 |
| CpGb-eMAL6g | 121 | 118 |
| CpGb-eMAL61 | 117 | 114 |

TABLE 3

Relative gas production in dough of strains A and C, transformed with 2μ derived plasmids peG418 and pGb-eMAL6g, $CO_2$ production was corrected to 285 mg dry matter.

| Strains | 60 minutes | 100 minutes | 120 minutes | 165 minutes |
|---|---|---|---|---|
| ApeG418 | 100 | 100 | 100 | 100 |
| ApGb-eMAL6g | 125 | 125 | 125 | 121 |
| CpeG418 | 100 | 100 | 100 | 100 |
| CpGb-eNAL6g | 151 | 141 | 138 | 129 |

EXAMPLE 2

$CO_2$ production of yeast strains transformed with integrating plasmids containing recombinant maltase and/or maltose permease genes.

Parental yeast strain A was transformed with pGb-iA32/G418 (ADHI/maltose permease; see FIG. 6) and pGb-iRRol (ADHI/maltose permease and EFIαA/maltase; see FIG. 7).

Parental strain A and both integrative transformants were grown fed batchwise on molasses similar to the commercial aerobic fermentation (see Table 1). After harvesting the cells, $CO_2$ production is measured in a standard dough test with no sugar added. The gas production, as analyzed in this test, is summarized in Table 4. Integration of pGb-iA32/G418 into the chromosome of strain A improves gas production in dough significantly. The relative improvement varies somewhat depending on time of measurement (see Table 4). When in addition to an altered maltose permease gene an altered maltase gene is integrated in the chromosome of commercial strain A using pGb-iRRol, gassing power is even further improved. In this typical experiment about 30% more $CO_2$ is produced after 165 minutes in a lean dough, which corresponds to a level of about 410 ml $CO_2$/285 mg dry weight of yeast.

The obtained improvement in leavening activity is maintained during keeping at 23° C. The loss of leavening activity during keeping is virtually identical for parental strain A and the novel strains (see Table 5).

TABLE 4

Relative gas production of strain A and its rDNA derivatives provided with altered maltase and/or maltose permease genes. Gas values have been corrected to 285 mg dry matter. No sugar was added to the dough.

| Strains | 60 minutes | 100 minutes | 120 minutes | 165 minutes |
|---|---|---|---|---|
| A | 100 | 100 | 100 | 100 |
| ApGb-iA32/G418 | 113 | 115 | 115 | 111 |
| ApGb-iRRol | 131 | 136 | 138 | 133 |

TABLE 5

Keeping quality of strain A and its rDNA derivatives provided with altered maltase and/or maltose permease genes. Leavening activity was measured as in Table 4 after keeping of compressed yeast at 23° C. for 4 days.

| Strain | Keeping quality (% of original leavening activity) |
|---|---|
| A | 90 |
| ApGb-iA32/G418 | 91 |
| ApGb-iRRol | 88 |

EXAMPLE 3

Enzyme activities and substrate uptake rates of yeast strains transformed with integrating plasmids containing recombinant maltase and/or maltose permease genes.

As described above, the expression of maltose permease and maltase is subject to maltose induction and glucose repression. This phenomenon is shown in FIG. 8 for wild-type cells of strain A. Specific activities of maltose permease and maltase do not increase until most of the glucose has been utilized.

The activity of maltose permease at the onset of dough-rise is increased by introduction of an altered maltose permease gene into the yeast genome (strain ApGb-iA32/G418) as shown in FIG. 9.

Surprisingly, activities of maltase were increased as well in this construct (FIG. 10). This novel strain ApGb-iA32/G418 fermented maltose more rapidly than the parental strain A in medium A which contains maltose as the main carbon and energy source (FIG. 11). In medium B containing glucose as the main carbon and energy source this effect was less pronounced in (FIG. 12).

In addition to an altered maltose permease gene, an altered maltase gene was integrated into the chromosome yielding strain ApGb-iRRol. This strain fermented maltose to $CO_2$ and ethanol at an even higher rate in medium A (FIG. 11) and also in medium B (FIG. 12). Despite the high extracellular concentration of glucose considerable amounts of maltose were metabolized by this novel strain. Strain ApGb-iRRol exhibited higher specific activities of maltase and maltose permease during dough-rise than parental strain A and strain ApGb-iA32/G418 (FIGS. 9 and 10).

It is evident from the above results, that improved yeast strains can be achieved by introduction of genes from a MAL locus, either individually or in combination. Thus, much more efficient fermentation may be achieved with more rapid ethanol and carbon dioxide production and utilization of maltose as an alternative carbon source. Furthermore, by changing the promoters from the natural promoters to other promoters which may act constitively under the conditions of the fermentation and are "strong" promoters in providing for a high rate of transcription, greatly improved leavening of dough may be achieved, both in lean and sweet doughs. In addition, the modified yeast strains may be used in both lean and sweet doughs, rather than requiring different strains, depending upon the nature of the strain.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A transformed yeast capable of enhanced production of carbon dioxide as compared to an untransformed parent of said yeast upon fermentation in a medium comprising maltose, wherein said maltose is fermentable by both said parent and said transformed yeast, and wherein said transformed yeast comprises a DNA construct comprising at least one gene capable of expression in said transformed yeast encoding a maltose permease, maltase or a maltose regulatory protein.

2. A yeast according to claim 1, wherein said construct comprises at least two said genes.

3. A yeast according to claim 1, wherein transcription of said gene is regulated by a transcriptional inititation region foreign to said gene.

4. A yeast according to claim 1, wherein said gene is under the transcriptional initiation control of the yeast alcohol dehydrogenase I promoter or yeast translation elongation factor promoter.

5. A yeast according to claim 1, wherein said construct is a portion of a plasmid stable in said yeast.

6. A yeast according to claim 1, wherein said construct is integrated into a chromosome of said yeast.

7. A yeast according to claim 1, wherein said construct is free of prokaryotic DNA.

8. A yeast according to claim 1, wherein said yeast is of the species Saccharomyces cerevisisae.

9. A transformed yeast capable of enhanced fermentation of maltose into ethanol and carbon dioxide as compared to an untransformed parent yeast capable of fermenting maltose wherein said transformed yeast comprises a DNA construct comprising at least one of a gene encoding maltase, maltose permease or a maltose regulatory protein, wherein transcription of at least one of said genes is regulated by a constitutive promoter functional in yeast and wherein said DNA construct is free of prokaryotic DNA.

10. A yeast according to claim 9, wherein said promoter is a yeast promoter and comprises an alcohol dehydrogenase I promoter or a translation elongation factor-1 or -2.

11. A yeast according to claim 10, wherein said yeast promoter is a Saccharomyces promoter.

12. A yeast according to any of claims 1-11 having a moisture content of 4 to 8%.

13. The transformed yeast according to claim 1, wherein said gene is homologous to said host.

14. The transformed yeast according to claim 1, wherein said gene is a chimeric gene.

15. The transformed yeast according to claim 14, wherein the promoter of said chimeric gene is a constitutive promoter.

16. A yeast according to claim 1, wherein said medium is flour or dough.

17. A transformed yeast capable of enhanced production of carbon dioxide as compared to an untransformed parent upon fermentation under anaerobic conditions in a medium comprising maltose, wherein said maltose is fermentable by both said parent and said transformed yeast, and wherein said transformed yeast comprises a DNA construct comprising at least one gene capable of expression in said transformed yeast encoding a maltose permease, maltase or a maltose regulatory protein.

18. A yeast according to claim 17, wherein said fermentation under anaerobic conditions comprises fermentation in dough.

19. A Saccharomyces cerevisiae strain selected form the group consisting of:
A-pGb-iA32/G418; A-pGb-iRRol; A-pGb-eMAL6g; A-pGb-eMAL61; A-pGb-eMAL63; and C-pGb-eMAL6g.

20. A plasmid selected from the group consisting of: pGb-iA32/G418; pGb-iRRol; pGb-eMAL6g; pGb-eMAL61; pGb-eMAL63; and pGb-M6g(delta-9).

* * * * *